United States Patent [19]

Rasmussen

[11] 4,093,811

[45] June 6, 1978

[54] 2-ARYL-4-CYANOMETHYL-5-METHYLIMIDAZOLES

[75] Inventor: Chris Royce Rasmussen, Ambler, Pa.

[73] Assignee: McNeil Laboratories, Incorporated, Ft. Washington, Pa.

[21] Appl. No.: 692,268

[22] Filed: Jun. 3, 1976

Related U.S. Application Data

[63] Continuation of Ser. No. 483,251, Jun. 26, 1974, abandoned.

[51] Int. Cl.$^2$ .......................................... C07D 233/64
[52] U.S. Cl. ...................................... 548/342; 424/57; 424/273 R; 548/351
[58] Field of Search ........................ 260/309; 548/342

[56] References Cited

FOREIGN PATENT DOCUMENTS 42-1546  1/1964  Japan ..................................... 260/309

OTHER PUBLICATIONS

Cornforth et al., J. Chem. Soc. (London) 1948, pp. 731–735.
Dziuron et al., I Chem. Abst. 1973, vol. 79, No. 78689g.
Dziuron et al., II Arch. Pharm. 1974 (Jan. 1974) vol. 307, pp. 89–95.
Diels et al., Berichte 1916, vol. 49, pp. 1711–1721.
Ewins, Chem. Abst., 1912, vol. 6, pp. 742–743.
Lawson; J. Chem. Soc. (London) 1957, pp. 4225–4228.
Ruoff et al., J. Amer. Chem. Soc., 1950, vol. 72, pp. 4950–4953.

*Primary Examiner*—Natalie Trousof
*Attorney, Agent, or Firm*—Salvatore R. Conte

[57] ABSTRACT

Novel 2-aryl-4-cyanomethyl-5-methylimidazoles useful for their ultra-violet (U.V.) absorbing properties, and certain novel precursors therefor. The species, 2-cyanomethyl-5-methyl-4-phenylimidazole, also has cerebral vasodilating activity.

8 Claims, No Drawings

2-ARYL-4-CYANOMETHYL-5-METHYLIMIDAZOLES

This is a continuation of application Ser. No. 483,251 filed June 26, 1974, now abandoned.

DESCRIPTION OF THE INVENTION

The invention relates to novel 2-aryl-4-cyanomethyl-5-methylimidazoles having the following formula:

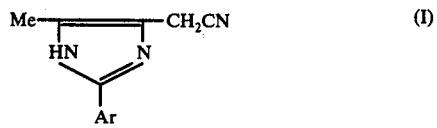

and mineral acid addition salts thereof, wherein Ar is a member selected from the group consisting of phenyl, methylenedioxyphenyl, loweralkanoylphenyl, loweralkylthiophenyl and phenyl substituted with 1 to 3 members selected from the group consisting of loweralkyl, loweralkoxy, halo, hydroxy, phenoxy and nitro.

As used herein, the prefix "lower" designates a 1 to 8 carbon content or the particular group it modifies; and the term "halo" represents chloro, bromo, fluoro and iodo. Typical mineral acids are the hydrohalic acids and nitric, sulfuric and the like acids.

The subject compounds (I) are prepared by reacting an appropriate benzamidine of formula (II), wherein Ar is as previously defined, with biacetyl (III) in a suitable lower alkanol, such as isopropanol and tert-butanol, to yield 2-Ar-4-loweralkoxymethyl-5-methylimidazole (IV). Elevated temperatures may be employed to enhance the rate of reaction and refluxing conditions are preferred. Use of the benzamidine (II) in the form of a mineral acid addition salt will afford the corresponding acid addition salt of (IV). The ester function of (IV) is then cleaved by heating with a strong non-oxidizing mineral acid, such as, for example, HCl, HBr, H$_2$SO$_4$ and the like, to yield the corresponding 4-hydroxymethyl derivative (V). If desired, conventional treatment with alkali may be employed to convert the acid addition salt form of (V) to the corresponding base form. Subsequent transformation of the hydroxy function in (V) to a chloro function is then accomplished by treating (V), either in base or in the form of an acid addition salt, with a chlorinating agent, for example, thionyl chloride, in a suitable non-polar aprotic organic solvent, for example, an aromatic hydrocarbon such as benzene, toluene, xylene and the like; a halogenated hydrocarbon such as chloroform, methylene chloride and the like; and an ether such as tetrahydrofuran, dioxane and the like. The thus-obtained 2-Ar-4-chloromethyl-5-methylimidazole (VI) is then subjected to standard chloro-to-nitrile transformation, for example, by treatment with excess sodium cyanide in a solvent such as dimethylsulfoxide (DMSO). The foregoing reactions may be schematically illustrated as follows:

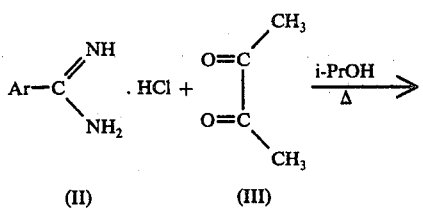

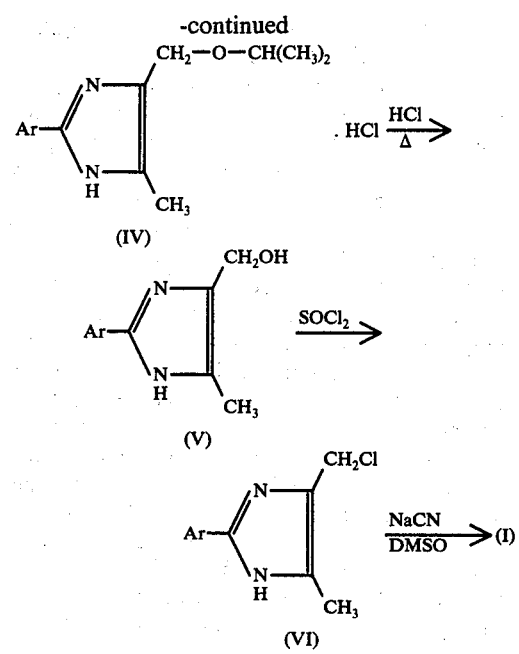

The foregoing intermediates are obtainable in free base form or in the form of an acid addition salt depending upon the particular isolation conditions employed. The free bases are readily convertible to the salt form by standard treatment with a mineral acid and the salts in turn are readily convertible to the free base form by standard treatment with alkali.

The benzamidine precursors (II) and methods for their preparation are described in the literature. The following compounds of formula (I) are representative of those contemplated by this invention and which may be prepared according to the procedures herein described:

4-cyanomethyl-5-methyl-2-m-nitrophenylimidazole;
4-cyanomethyl-5-methyl-2-p-methylthiophenylimidazole;
2-(2,4-dibromophenyl)-4-cyanomethyl-5-methylimidazole;
4-cyanomethyl-2-(2-ethyl-4-isopropoxyphenyl)-5-methylimidazole;
2-(p-n-butoxyphenyl)-4-cyanomethyl-5-methylimidazole;
4-cyanomethyl-2-p-fluorophenyl-5-methylimidazole;
2-(p-acetylphenyl)-4-cyanomethyl-5-methylimidazole;
4-cyanomethyl-2-(3,4-dimethylphenyl)-5-methylimidazole;
4-cyanomethyl-2-p-butylphenyl-5-methylimidazole;
4-cyanomethyl-2-(2,4,6-trimethylphenyl)-5-methylimidazole;
2-(2,4,6-trichlorophenyl)-4-cyanomethyl-5-methylimidazole;
4-cyanomethyl-2-p-propionylphenyl-5-methylimidazole;
4-cyanomethyl-2-(3,4,5-trimethoxyphenyl)-5-methylimidazole; and
2-(2-chloro-4-methylphenyl)-4-cyanomethyl-5-methylimidazole.

The subject compounds (I), particularly in the form of the free base, strongly absorb ultra-violet (U.V.) light, generally above 280 nm, and are useful as U.V.-screening materials, for example, in plastic products and sunburn preventive formulations. Because of their general solubility in organic materials, the bases may be used as U.V.-absorbers in plastics and resins such as, for example, polystyrene, polyethylene, polypropylene, polyacrylics (e.g., methacrylate resins, polyacrylamides, polyacrylonitrile fibers, etc.), polamide (e.g., nylon) fibers, and polyester fibers. The inclusion of about 0.01–5.0 percent of the absorber, based on the polymer weight, is usually sufficient to render protection against U.V. light, such as in plastic films, light filters, etc. The absorber may be incorporated into the mixture of monomers before polymerization to form the polymer or it may be incorporated into the polymer at other stages during its handling, as by milling into the polymer together with other compounding ingredients, or during the spinning of the polymer into fibers, etc.

The acid addition salts of (I), which are more water-soluble than the base form, are preferably employed as sunscreening agents in typical hydrophylic types of antisunburn formulations in amounts of about 0.1–5.0 percent by weight (see G. W. van Ham & W. P. Herzog, Chapter 6, "The Design of Sunscreen Preparations", in "Drug Design IV", E. J. Ariens, Ed., Academic Press, N.Y. and London, 1973.

The most preferred compound is 2-cyanomethyl-5-methyl-4-phenylimidazole, which, in addition to its U.V.-absorbing characteristic, has been found to possess useful pharmacological properties. For example, in tests on laboratory animals (see Example VIII), at doses ranging from about 2.5 to about 10 mg/kg body weight, this compound, in base form or in the form of its therapeutically active acid addition salts, exhibits cerebral vasodilating activity, which is useful in the treatment of cerebral bloodflow insufficiency, e.g., in senility. It also elicits an increase in the efficiency of the heart as shown by a lowering of the myocardial oxygen consumption without compromising heart work, which is useful in the treatment of angina pectoris.

An alternative method of preparing the preferred compound, 4-cyanomethyl-5-methyl-2-phenylimidazole (X), is from the precursor, 4,5-dimethyl-2-phenylimidazoline-4,5-diol (VII), preferably in the form of a mineral acid addition salt. The precursor (VII), which is described by O. Diels and K. Schleich, Ber. 49, 1711 (1916), may be obtained by the reaction of benzamidine with biacetyl in water. By heating (VII) in a strong non-oxidizing mineral acid, preferably dilute HCl, under reflux conditions (about 95° C) for about 1–2 hours, and then cooling the reaction mixture to about 0° C for maximal precipitation conditions, there is obtained 5(4)-methyl-2-phenylimidazole-4(5)-methanol (VIII), the hydroxy function of which is then transformed successively to the chloride (IX) and then to the nitrile (X) as previously described, to yield the desired 4-cyanomethyl-5-methyl-2-phenyl-imidazole. The foregoing reactions may be illustrated by the following schematic flow chart:

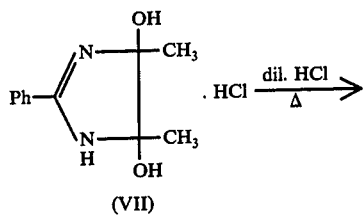

(VII)

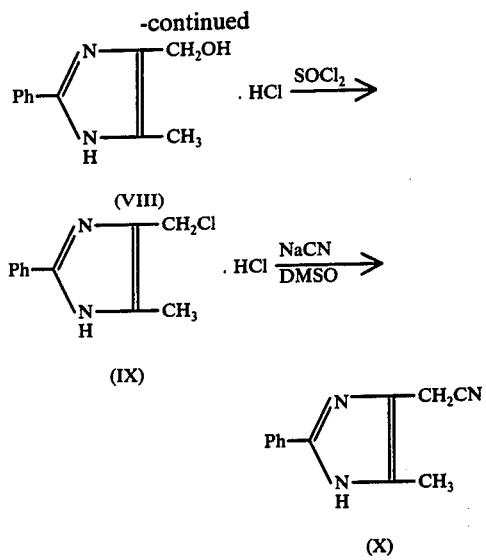

The preferred compound (X) may be converted to therapeutically active non-toxic acid addition salts by treatment with an appropriate acid, such as, for example, an inorganic acid, such as, a hydrohalic acid, e.g., hydrochloric, hydrobromic or hydroiodic acid, and sulfuric acid, nitric acid, phosphoric acid and the like; or an organic acid, such as, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicyclic, p-aminosalicylic, 2-phenoxybenzoic, 2-acetoxybenzoic and the like acids. Conversely, the salt form can be converted by treatment with alkali into the free base form.

The isopropoxymethyl derivatives of formula (IV), the hydroxymethyl derivatives of formula (V) and the chloromethyl derivatives of formula (VI), wherein Ar is other than phenyl, are deemed to be novel and, in view of their utility as precursors for synthesizing the compounds of formula (I), such novel derivatives constitute an additional feature of this invention.

The following examples are intended to illustrate, but not to limit, the scope of the present invention.

EXAMPLE I

A.

4-Isopropoxymethyl-2-(p-methoxyphenyl)-5-methylimidazole Hydrochloride

To a solution of 38.4 g (0.206 mole) of p-methoxybenzamidine hydrochloride in 1 liter of refluxing isopropyl alcohol is added 25 g (0.25 mole) of biacetyl. The mixture is stirred and refluxed for 72 hours. The solvent is removed to dryness under reduced pressure and the solid residue taken up in fresh hot isopropyl alcohol. Ether is added and, on chilling, pale yellow crystals form which are collected to give about 49.5 g (81% yield) of 4-isopropoxymethyl-2-(p-methoxyphenyl)-5-methylimidazole hydrochloride as very pale yellow crystals, m.p. 149°–150° C (dec.). Recrystallization twice from isopropyl alcohol-ether with charcoaling gives the product as white crystals, m.p. 149°–150° C (dec.).

B.
4-Hydroxymethyl-2-(p-methoxyphenyl)-5-methylimidazole Hydrochloride

A mixture of 4-isopropoxymethyl-2-(p-methoxyphenyl)-5-methylimidazole hydrochloride (48.9 g, 0.164 mole) in 500 ml of water is stirred and refluxed. To this mixture is added 50 ml of concentrated hydrochloric acid and stirring and refluxing are continued for 4 hrs. The mixture is then chilled and filtered to give about 39.5 g (94%) of 4-hydroxymethyl-2-(p-methoxyphenyl)-5-methylimidazole hydrochloride which is recrystallized from isopropyl alcohol, m.p. 146°–148° C (dec.). Treatment with alkali (e.g., NaOH) affords the corresponding base form.

C.
4-Cyanomethyl-2-(p-methoxyphenyl)-5-methylimidazole

To a stirred slurry of 15.3 g (0.06 mole) of 4-hydroxymethyl-2-p-methoxyphenyl-5-methyl-imidazole hydrochloride in 200 ml of chloroform are added 15 g (0.12 mole) of thionyl chlorine in $CHCl_3$. Vigorous evolution of gas is observed during the addition. The reaction mixture is stirred at room temperature for 5 hours, during which time the slurry dissolves to form a pale pink solution. The solvent is then removed under reduced pressure and the solid residue taken up in fresh $CHCl_3$. The solution is then filtered, ether is added until cloudy and then chilled. White crystals of 5-chloromethyl-2-p-methoxyphenyl-4-methyl-imidazole hydrochloride are precipitated, filtered and collected (91% yield), m.p. 203°–205° C (dec.). This chloromethyl derivative is dissolved in 75 ml of warm DMSO and added to a hot solution of 15 g (0.3 mole) of sodium cyanide in DMSO. The reaction mixture is stirred at room temperature for 16 hours and warmed to 60° C for 4 hours, then allowed to cool to room temperature and poured over 1 liter of ice and stirred. A yellow solid is precipitated, filtered and air-dried. Three recrystallizations from methylene chloride-hexane give the product, 4-cyanomethyl-2-(p-methoxyphenyl)-5-methyl-imidazole, as fluffy white crystals, m.p, 158°–160° C.

EXAMPLE II

A.
2-(p-Chlorophenyl)-4-isoprpoxymethyl-5-methylimidazole Hydrochloride

To a solution of 38 g (0.2) mole of p-chloro-benzamidine hydrochloride in 500 ml of refluxing isopropyl alcohol is added 25 g (0.25 mole) of biacetyl. The mixture is stirred and refluxed for 48 hours. The solvent is removed to dryness under reduced pressure. The solid residue is taken up in fresh, hot isopropyl alcohol, the solution filtered and ether added. On chilling, white crystals of 2-(p-chlorophenyl)-4-isopropoxymethyl-5-methyl-imidazole hydrochloride precipitate and are collected, about 52.9 g (88% yield), m.p. 174° C (dec.). Recrystallization from isopropyl alcohol-ether with charcoaling gives white crystals, m.p. 175° C (dec.).

B.
2-(p-Chlorophenyl)-4-hydroxymethyl-5-methylimidazole hydrochloride

A mixture of 2-(p-chlorophenyl)-4-isopropoxymethyl-5-methylimidazole hydrochloride (45.9 g, 0.152 mole) and 250 ml of water is stirred and refluxed. To this mixture is added 25 ml of concentrated hydrochloric acid and stirring and refluxing are continued for 6 hours. This mixture is chilled and filtered. The solid is dried in a vacuum desiccator and then recrystallized from isopropyl alcohol to give 25 g (64%) of 2-(p-chlorophenyl)-4-hydroxymethyl-5-methylimidazole hydrochloride, m.p. 181° C (dec.).

C.
2-(p-Chlorophenyl)-4-cyanomethyl-5-methyl-imidazole

To a stirred slurry of 10.4 g (0.04 mole) of 2-p-chlorophenyl-4-hydroxymethyl-5-methyl-imidazole hydrochloride in 250 ml of chloroform is added 10 g (0.08 mole) of thionyl chloride in $CHCl_3$. The reaction mixture is warmed to reflux for 6 hours with stirring and then cooled to room temperature. White crystals of 4-chloromethyl-2-p-chlorophenyl-5-methylimidazole hydrochloride in 98% yield, m.p., 224°–226° C (dec.) are obtained. This material is collected and dissolved in 50 ml of warm DMSO and added to a solution of 10 g (0.2 mole) of sodium cyanide in 150 ml of hot DMSO. The mixture is warmed to 60° C for 16 hours and then stirred at room temperature for 16 hours. The reaction mixture is poured over 1 liter of ice and stirred. The tan solid that forms is filtered, collected and air-dried. The crude solid is taken up in 2 liters of ether, charcoaled and filtered. Concentration on a steam bath with hexane addition yields pale green crystals of product. Additional recrystallizations from ether-hexane and methylene chloridehexane gives about 4.5 g (49%) of pale yellow crystals of 2-(p-chlorophenyl)-4-cyanomethyl-5-methyl-imidazole, m.p., 163° – 165° C. Treatment with a mineral acid, e.g., hydrochloric, nitric, sulfuric and the like, affords the corresponding acid addition salts.

EXAMPLE III

4,5-Dimethyl-2-phenylimidazoline-4,5-diol Hydrochloride

To 56.4 g (0.323 mole) of benzamidine hydrochloride hydrate in 200 ml of warm water is added with vigorous stirring 40 ml of biacetyl. Within a few minutes a heavy precipitate forms and 150 ml of isopropyl alcohol is added followed by 5.0 g of sodium acetate hydrate dissolved in 15 ml of warm water. Stirring is continued for 4 hours after which time the product, 4,5-dimethyl-2-phenylimidazoline-4,5-diol hydrochloride, is filtered off and washed with isopropyl alcohol. Recrystallization from 95% ethanol gives the pure product, m.p. 162°–165° C (dec.).

EXAMPLE IV

4(5)-Hydroxymethyl-5(4)-methyl-2-phenylimidazole Hydrochloride

One liter of hydrochloric acid (10%) is preheated almost to boiling. With vigorous stirring, 103.8 g (0.427 mole) of 5,6-dimethyl-2-phenyl-imidazoline-5,6-diol hydrochloride is added. The mixture is stirred and refluxed gently for about 1 hr with all of the starting material dissolved. The temperature is maintained at about 95° C for an additional hour, at which time the mixture is cooled in an ice-bath. The product, 4(5)-hydromethyl-5(4)-methyl-2-phenylimidazole hydrochloride, crystallizes upon cooling and is collected and recrystallized from water (min. amount). Drying in vacuo overnight (about 15 hours) gives the pure product, m.p. 166°–168° C (dec.).

EXAMPLE V

4-Chloromethyl-5-methyl-2-phenylimidazole Hydrochloride

To a suspension of 3.76 g (0.02 mole) of 4(5)-hydroxymethyl-5(4)-methyl-2-phenylimidazole hydrochloride in 9.4 ml dry benzene is added 9.4 ml thionyl chloride over 1 minute. The reaction mixture becomes homogeneous. After warming on a steam bath under reflux for about 5 minutes, the product, 4-chloromethyl-5-methyl-2-phenylimidazole hydrochloride, precipitates. After cooling, the crude product is filtered, washed with dry benzene and air-dried, m.p. 197°–207° C. The product may be used without further purification in preparing the corresponding 4-cyanomethyl derivative. Treatment with alkali (e.g., NaOH) affords the corresponding base form.

EXAMPLE VI

4-Cyanomethyl-5-methyl-2-phenylimidazole

A solution of 48.6 g (0.2 mole) of 4-chloromethyl-5-methyl-2-phenylimidazole hydrochloride [see Cornforth & Huang, J. Chem. Soc., 731 (1948)] in 200 ml of DMSO is added (over 20 minutes) to a rapidly stirred solution of sodium cyanide, prepared by dissolving 29.4 g (0.6 mole) of sodium cyanide in 70 ml of water and adding 200 ml of DMSO, at 0° to 5° C. [slightly modified procedure of W. Schultze, J. Prakt. Chem. 19, 91-100 (1922)]. The reaction mixture is stirred in the cold for 2 hours and then poured onto a slight excess of cracked ice which causes a semicrystalline gum to separate (Crop A). The gum is quickly filtered off and to the filtrate is added sufficient aqueous sodium carbonate (10%) to give a volume of 2 liters. The mixture is allowed to stand overnight during which time a second crop (about 12-13 g) crystallizes (Crop B). Extraction of the mother liquor with ethyl acetate gives an aditional (about 2-3 g) yield (Crop C). Crop A is recrystallized from benzene-Norite B. Crop C is recrystallized from benzene. The resulting crystals are combined with Crop B. Repeated recrystallizations from benzene gives a pure product of 4-cyanomethyl-5-methyl-2-phenylimidazole, m.p., 132°–140° C. Treatment with a mineral acid, e.g., sulfuric, hydrobromic and the like, affords the corresponding acid addition salts.

EXAMPLE VII

The procedure of Example I is followed except that an equivalent amount of an appropriately substituted benzamine HCl is substituted for the p-methoxy-benzamidine HCl used therein to yield the following respective products:

2-(3,5-dichlorophenyl)-4-cyanomethyl-5-methylimidazole;
4-cyanomethyl-2-(3,5-dimethoxyphenyl)-5-methylimidazole;
4-cyanomethyl-5-methyl-2-p-n-octylphenylimidazole;
4-cyanomethyl-5-methyl-2-(3,4-methylenedioxyphenyl)-imidazole;
2-p-butylthiophenyl-4-cyanomethyl-5-methylimidazole;
4-cyanomethyl-2-(4-hydroxy-3,5-diiodophenyl)-5-methylimidazole;
4-cyanomethyl-5-methyl-2-p-phenoxyphenylimidazole;
2-(3-chloro-4-phenoxyphenyl)-4-cyanomethyl-5-methylimidazole; and
4-cyanomethyl-2-(4-hydroxy-3-nitrophenyl)-5-methylimidazole.

EXAMPLE VIII

A. Pig-tail monkeys (macaca mernestrina) and rhesus monkeys (macaca mulatta), male and female, are anesthetized with 4 mg/kg i.v. of phencyclidine followed by 20-30 mg/kg i.v. of pentobarbital sodium. The trachea is exposed and cannulated to maintain a patent airway. The left common carotid artery is isolated centrally to expose its internal and external branches. The external carotid branch is ligated and an electromagnetic flow probe (Statham-Medicon) is placed around the common carotid artery for measurement of internal carotid artery blood flow. In the monkey, blood flow perfusing the internal carotid artery supplies primarily the brain since few extra-cerebral anastomotic channels exist. The left external iliac artery is isolated and another electromagnetic flow probe placed around it to measure changes in peripheral blood flow. The contra-lateral femoral artery and vein are isolated and catheterized for recording of femoral arterial pressure and for intravenous injection respectively. In several animals arterial blood samples are obtained from the catheterized femoral artery and from a catheter placed cephalad into the internal jugular vein with its tip located in the area of the jugular bulb. Arterial-venous oxygen differences are determined by standard equipment, for example a Beckman Physiological Gas Analyzer, Model 160 (Beckman Instruments, Inc., Spinco Division, Palo Alto, California). A decrease in arterial-venous oxygen content (increase in venous oxygen, no change in arterial oxygen) indicates increased oxygen delivery. With the compound, 2-cyanomethyl-5-methyl-4-phenylimidazole, the maximum increase in cerebral blood flow in the rhesus monkey, at 5 mg/kg i.v., is about 50% of that shown by a 90:10 mixture of $O_2:CO_2$. Such mixtures are known to be cerebral vasodilators [Ketz and Schmidt, J. Clin. Invest., 27, 484–492 (1948]. In pig-tail monkeys the maximum effect is about 100% of said $O_2:CO_2$ mixture at the same dose of compound.

B. When the compound, 2-cyanomethyl-5-methyl-4-phenylimidazole, is administered at 5 mg/kg i.v. in the dog heart-lung experiment described by Markowitz et al., Experimental Surgery, Williams and Wilkins Co., Baltimore, Md., p. 369 (1964), the same heart work (cardiac output x aortic pressure) is performed while less oxygen (statistically significant) is consumed by the myocardium, thereby improving the efficiency of the heart.

What is claimed is:

1. A compound selected from the group consisting of 2-aryl-4-cyanomethyl-5-methylimidazole having the formula:

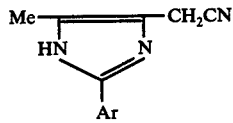

and mineral acid addition salts thereof, wherein Ar is a member selected from the group consisting of phenyl, methylenedioxyphenyl, loweralkanoylphenyl, loweralkylthiophenyl and phenyl substituted with 1 to 3 members selected from the group consisting of loweralkyl, loweralkoxy, halo, hydroxy, phenoxy and nitro.

2. A compound selected from the group consisting of 4-cyanomethyl-2-loweralkoxyphenyl-5-methylimidazole and mineral acid addition salts thereof.

3. 4-Cyanomethyl-2-(p-methoxyphenyl)-5-methylimidazole.

4. A compound selected from the group consisting of 4-cyanomethyl-2-halophenyl-5-methylimidazole and mineral acid addition salts thereof.

5. 2-(p-Chlorophenyl)-4-cyanomethyl-5-methylimidazole.

6. A compound selected from the group consisting of 4-cyanomethyl-5-methyl-2-phenylimidazole and therapeutically active acid addition salts thereof.

7. 4-Cyanomethyl-5-methyl-2-phenylimidazole.

8. A compound selected from the group consisting of 2-aryl-4-isopropoxymethyl-5-methylimidazole having the formula:

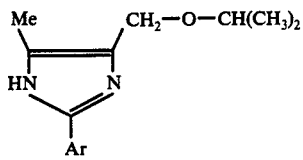

and the mineral acid addition salts thereof, wherein Ar is a member selected from the group consisting of methylenedioxyphenyl, loweralkanoylphenyl, loweralkylthiophenyl and phenyl substituted with 1 to 3 members selected from the group consisting of loweralkyl, loweralkoxy, halo, hydroxy, phenoxy and nitro.

* * * * *